United States Patent [19]

Hitzeman et al.

[11] Patent Number: 4,865,989
[45] Date of Patent: Sep. 12, 1989

[54] EUKARYOTIC VECTORS AND PLASMIDS HAVING PGK REGULATORY SIGNALS

[75] Inventors: Ronald Hitzeman, Pacifica; John A. Carbon, Santa Barbara, both of Calif.

[73] Assignee: U.C. Regents, Alameda, Calif.

[21] Appl. No.: 110,559

[22] Filed: Oct. 20, 1987

Related U.S. Application Data

[63] Continuation of Ser. No. 333,341, Dec. 22, 1981, which is a continuation-in-part of Ser. No. 325,268, Nov. 27, 1981.

[51] Int. Cl.⁴ .................. C12N 1/00; C12N 15/00
[52] U.S. Cl. ..................... 435/320; 435/172.3; 935/28; 935/37
[58] Field of Search .............. 435/172.3, 68, 70, 320; 935/28, 37

[56] References Cited

PUBLICATIONS

Legerski et al, Nucleic Acids Research, vol. 5 pp. 1445–1464 (1978).
Scheller et al, Science, vol. 196, pp. 177–180.
Ratzkin et al, PNAS U.S.A., vol. 74 pp. 487–491 (1977).
Hinnen et al, PNAS U.S.A., vol. 75 pp. 1929–1933.
Hitzeman et al, The Journal of Biological Chemistry, vol. 255, No. 24, pp. 12073–12080 Dec. 25, 1980.
Ilgen et al, Genetic Engineering Ed by Setlow et al, Plenum Press, New York, pp. 117–131 (1979).
Stouhl et al, Proc. Natl. Acad. Sci. U.S.A., vol. 76, No. 3, pp. 1035–1039 Mar. 1979.
Gray et al, Nucleic Acids Research vol. 2, pp. 1459–1492 (1975).
Chen, et al. (1984) Nucleic Acids Research, 12:8951–8970.
Derynck, et al. (1983) Experimental Manipulation of Gene Expression, Chapter 13:247–258.
Hitzeman et al. (1983) Science, vol. 219:620–625.
Hitzeman et al. "Recombinant DNA Products", CRC Press, Chapter 3:47–65.
Mellor et al. (1983) Elsevier Science Publishers B.V. Gene, 24:1–14.
Singh et al.(1983) Genetics:New Frontiers, 168–177.

*Primary Examiner*—Alvin E. Tanenholtz
*Attorney, Agent, or Firm*—Bertram I. Rowland; Barbara Rae-Venter

[57] ABSTRACT

Novel compositions and methods employing the compositions are provided involving eukaryotic plasmids having a replication system or replicon from an extrachromosomal element, a chromosomal replicator, and the regulatory signals of the structural gene for yeast 3-phosphoglycerokinase controlling expression of a structural gene. The plasmids find particular use in yeast for production of poly(amino acids).

19 Claims, 1 Drawing Sheet

EUKARYOTIC VECTORS AND PLASMIDS HAVING PGK REGULATORY SIGNALS

This invention was made with Government support under Grant No. CA-111034 awarded by the Department of Health and Human Services. The Government has certain rights in this invention.

CROSS-REFERENCE TO RELATED APPLICATION

This application is a file wrapper continuation of application Ser. No. 333,341, filed Dec. 22, 1981, which is a continuation-in-part of application Ser. No. 325,268, filed Nov. 27, 1981, which disclosure is incorporated herein by reference.

BACKGROUND OF THE INVENTION

1. Field of the Invention

The ability to reorient DNA segments to provide for expression of heterologous genes in microorganisms provides numerous opportunities to synthesize peptides of physiological and commercial interest. In most instances, it will be desirable to maximize the production of the protein or peptide of interest while still maintaining cell viability. A number of different ways can be employed to improve the production of a desired poly(amino acid) product. For example, by employing plasmids having high copy numbers, the number of genes which are being expressed will also be multiplied. Another technique is to use the regulatory genes involved with expression of a structural gene which codes for a poly(amino acid) which is produced in high yield. Other techniques may also be available, such as increasing the lifetime of the messenger RNA, enhancing the transcription of the DNA by employing activators, enhancing ribosomal binding, or the like.

2. Description of the Prior Art

Hitzeman, Clarke and Carbon (1980) J. Biol. Chem 255: 12073-12080 describe a plasmid having a yeast 3-phosphoglycerokinase PGK gene and accompanying regulatory signals capable of expression in yeast. Gray et al. (1975) Nucleic Acid Research 2: 1459-1492 and Legerski et al. ibid 5: 1445-1464 describe the properties and use of the double stranded exonuclease BAL 31. Scheller et al. (1977) Science 196: 177-180 describe the use of linkers having restriction sites. Complementation with a leu gene in bacteria and yeast is described by Ratzkin and Carbon (1977) PNAS USA 74: 487-491 and Hinnen et al. (1978) ibid 75: 1929-1933, respectively.

SUMMARY OF THE INVENTION

Novel plasmids are provided having a eukaryotic extrachromosomal replication system, desirably, in addition, a chromosomal replicator, and the regulatory sequences of the yeast PGK gene. Stable replication of the plasmid is obtained in a eukaryotic host with high yields of the expression product of the structural gene.

DESCRIPTION OF THE SPECIFIC EMBODIMENTS

Figure 1:
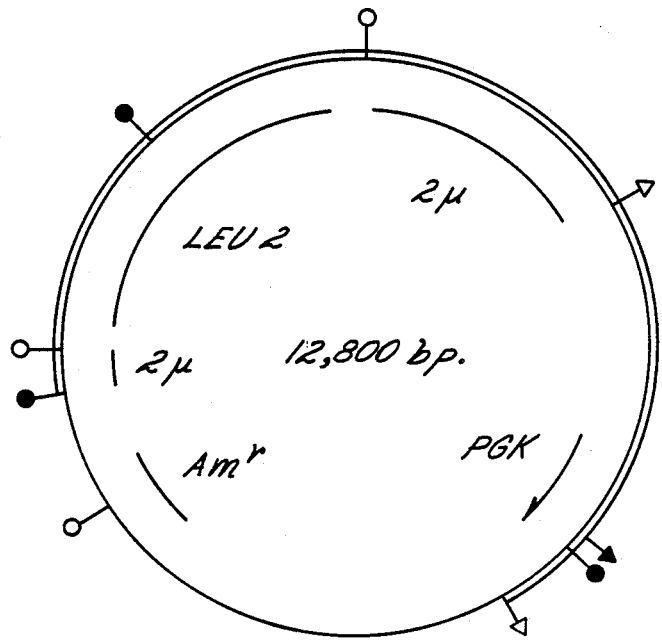
FIG. 1 is a depiction of plasmid pY9.

Novel eukaryotic vectors are provided for insertion and expression of structural genes in high yield in eukaryotic organisms. Particularly, the vector will have an extrachromosomal replication system, desirably a high copy number system, the regulatory signals of the yeast PGK structural gene, a structural gene including a ribosomal start site and under transcriptional control of the PGK regulatory genes and desirably a chromosomal replicator. In addition, other replication systems, regulatory genes, and structural genes may also be present in the vector for a variety of purposes.

In describing the plasmid, the various functional regions will first be discussed followed by the manner in which they may be joined together to provide for a vector having the desired properties for high yield expression of a desired peptide product.

The eukaryotic extrachromosomal replicator may be derived from a variety of sources, such as plastid DNA, plasmid DNA, or viruses. However, in order to obtain multiple copies of the generated plasmid, it will usually be desirable to use the latter two sources, namely plasmids and viruses, more particularly plasmids. Of particular interest for yeast and other eukaryotic hosts is a replication system or replicon from the $2\mu$-plasmid. See Broach et al. (1979) Gene 8: 121-133. Other replication systems may also find use in particular situations.

Optionally, a chromosomal replicator may also be included. The chromosomal replicator appears to enhance the production of the desired peptide. The chromosomal replicator from yeast is described in Stinchcomb et al. (1979) Nature 282: 39-43. The chromosomal replicator may be free of any structural gene or joined to a structural gene such as TRP1 as is described in Stinchcomb et al., 1979.

The PGK regulatory signals can be introduced by employing a fragment containing the regulatory signals and gene. Specifically, a HindIII 3.1 kbp fragment includes the yeast regulatory signals and PGK structural gene as well as flanking regions. The entire fragment may be introduced into an appropriate insertion site of a vector having the other desired functional features followed by restriction at an available restriction site in the 3.1 kbp fragment, particularly at a site within the PGK structural gene.

By treatment of the resulting linear DNA units with a double stranded exonuclease for varying periods of time, varying numbers of base pairs downstream from the PGK regulatory signals may be removed. In this manner, the DNA may be chewed back toward and, as desired, into the leader region of the PGK gene, resulting in an appropriate site for ligation of linkers. The linkers serve as a source of a restriction site for ligatable ends to a structural gene, which will then be under the regulatory control of the PGK regulatory genes, particularly the PGK promoter. Of particular utility is the Pseudomonas exonuclease BAL 31.

A terminator is also provided for transcriptional control of the structural gene. By cleaving at a restriction site internal to the PGK gene and then chewing back with a double-stranded exonuclease, linear DNA units are obtained which retain both the promoter and terminator regions of the PGK structural gene, whose functions are balanced and will fulfill their natural functions for any structural gene inserted between them. Alternatively, the terminator can be supplied on a separator restriction fragment while a terminator other than the naturally occurring PGK terminator may be employed, this will usually PGK terminator may be employed, this will usually offer no advantage and such different terminator needs to be balanced with the PGK promoter.

Conveniently, in addition to the eukaryotic replication system, a prokaryotic replication system is also included. This provides for a shuttle vector, which allows for substantial amplification of the plasmid followed by purification. Thus, the plasmid employed for transformation of the eukaryotic host can be reasonably certain to have the desired structure and be substantially homogeneous.

Various vectors are available having prokaryotic replication systems, such as pBR322, pRK290 and pSC101. These vectors normally include besides the prokaryotic replication system, one or more markers which may be employed for selection of transformants and selective growth of transformants against the untransformed host. Markers can include biocide resistance, particularly to antibiotics, such as ampicillin, tetracycline, trimethoprim, chloramphenicol, and penicillin, toxins, such as colicin, and heavy metals, such as mercuric salts.

Alternatively, complementation may be employed providing auxotrophy to a prototrophic host. Various structural genes may be used, such as trp, his, leu, lac, rec, and the like.

Finally, phage insensitivity can be introduced into a host organism to permit selection by phage lysis of untransformed sensitive bacteria.

The same markers may suffice where both the prokaryotic and the eukaryotic organisms are able to express the marker. In most situations, this will not be feasible and different markers will be used for the eukaryotic host as distinct from those used for the prokaryotic host. That is, while the structural genes will be different, the functions may be the same as described above.

The replication system for the prokaryote will normally be derived from a naturally occurring plasmid, a phage or synthetically produced.

Also useful in the construction of the plasmids of this invention are linkers. Linkers are DNA sequences which can be ligated, usually by blunt ended ligation, and which have a DNA sequence defining a desired restriction site. Employing linkers, a restriction site may be introduced into the plasmid at a desired position in relation to a particular sequence or functional element. Normally, the restriction site will be one which will be unique to the resulting plasmid allowing for insertion of a desired DNA element at that site. A wide variety of restriction endonucleases are presently available, which cleave dsDNA to provide blunt ends or cohesive ends by providing a staggered cleavage.

In preparing preferred embodiments of the plasmids of the subject invention, a prokaryotic plasmid will be employed into which is inserted the appropriate eukaryotic replication system. As already indicated, a large number of prokaryotic plasmids have been reported and their restriction maps determined. Thus, the replication system may be inserted at an appropriate restriction site in the prokaryotic plasmid, followed by amplification in a prokaryotic host.

The amplified plasmid may then be isolated and further manipulated by insertion of additional functional features, such as a chromosomal replicator, eukaryotic markers, and the like. After each insertion, further amplification and purification of the plasmid may be performed. Into an appropriate restriction site of the resulting vector, the PGK regulatory genes and structural genes may now be inserted and the resulting plasmid used for transformation and amplification. After isolation of the desired plasmid, the PGK structural gene may be cleaved at a variety of restriction sites, for example a BglII, EcoRI, SacI, SacII, XbaI, KpnI, HincII or HhaI site. Alternatively, other restriction sites could be introduced by in vitro mutagenesis.

The resulting linear DNA units may then be digested with a double-stranded exonuclease for varying times, so that varying amounts of the PGK coding sequences may be removed and a linear DNA unit obtained, with the terminus proximal to the PGK promoter region and in the leader region of the PGK gene, that is, between the mRNA start point and the translational AUG start point.

Blunt-ended linkers which contain a unique restriction site may now be added to the linear units. After ligation of the linkers to the linear DNA units, the resulting DNA may be subject to reaction with the restriction enzyme specific for the restriction site present in the linkers to provide for linear DNA units. The DNA units may be used for transformation (after ligation into various plasmid vectors) and the resulting cloned plasmids isolated. Their ability to serve as vectors for expression of structural genes under the control of the PGK regulatory genes or promoter may then be determined. This can be conveniently done by employing a structural gene which complements an auxotrophic host, or by screening clones with labeled antibodies. After selection of the desired vectors, the structural gene may be excised and other structural genes introduced.

Other protocols may be employed for preparing the vector having the PGK regulatory signals. By sequencing the PGK promoter and leader sequence, after restriction cleavage within the PGK gene and chewing back, the DNA may be circularized, cloned and hybridized with probes for the desired region and for the region to be removed, selecting for the clones which properly hybridize.

As appropriate, synthetictechniques may be employed, where the DNA sequences are synthesized and inserted.

A wide variety of structural genes may be employed for the production of peptides, such as enzymes, protein hormones, novel protein structures, and the like. In addition, the vectokrs can be used for enhanced production of DNA of a particular structural gene, for cloning and subcloning, as well as for enhanced production of messenger RNA which can then be used for production of cDNA. The vectors find wide application because of their versatility in allowing for amplification in bacteria and for replication, transcription, and translation in eukaryotes, particularly yeast.

The following examples are offered by way of illustration and not by way of limitation.

EXPERIMENTAL PROCEDURES

Materials

Yeast phosphoglycerate kinase (3-phospho-D-glycerate-1-phosphotransferase) was obtained from Sigma as type IV containing 2640 units/mg of protein and was further purified by Sephadex G-100 chromatography to give a single sharp band on sodium dodecyl sulfateacrylamide gel electrophoresis. Restriction enzymes and T4 DNA ligase were from New England Biolabs. $^{125}$I-Sodium iodide was obtained in 50 mM NaOH from ICN. CNBr-activated Sepharose 4B was obtained from Sigma. The BAL 31 nuclease activity can be obtained by centrifugation of stationary phase cultures grown in AMS-4 minimal medium (Espejo et al. (1971) J. Mol. Biol. 56: 597–621) modified by the substitution of casamino acids for the Special Amino Acids Mixture, and the supernatants (12 L per batch) is concentrated about 50-fold in a 2 L Amicon pressure dialysis cell equipped with a UM-10 membrane filter, the concentrate dialysed against CAM buffer (0.1M NaCl, 5 mM each $MgSO_4$ and $CaCl_2$, 20 mM tris, 1 mM EDTA, pH8.1) and used directly as the source of nuclease activity.

Strains and Media

The following E. coli strains were used: JA221 ($hsdM^+$ $hsdR^-$ lacY leuB6 ΔtrpE5 recA1) and JA300 (thr leuB6 thi thyA trpC1117 $hsdM^-$ $str^R$) were constructed in our laboratory from previously existing strains; W3110 trpC1117 (Yanofsky et al., 1971 Genetics 69: 407–433) was obtained from R. Mosteller (University of Southern California); DF576 ($F^-$pgk-1 rpsL) (Thomson et al., 1979 J. Bacteriol. 137: 502–506) was obtained from D Fraenkel (Harvard University). Several yeast strains were also used: RH218 (a trp1 gal2 SUC2 mal CUPI) (Miozzari et al., 1978 J. Bacteriol. 134: 48–59) was obtained from D. Stinchcomb (Stanford University); SB5-6 (trp1 pgk) and SB5-8 (trp1 pgk ade2) were obtained from a cross of 528-2 (α ade2 pgk) (Lam and Marmur, 1977 ibid 69: 409–433) and RH218; SB-1225-A (α cdc10 trp1 leu2 adc1) was obtained from J. Carbon.

E. coli were grown on the following media: S-agar plates contained 32 g of tryptone, 5 g of NaCl, 15 g of Difco agar, and 0.2 g of NaOH in 1 liter of solution (pH 7.3 tio 7.4); M9 (minimal medium) and LB (rich medium) are described by Miller (Vogel and Bonner, 1956 J. Biol. Chem. 218: 97–106) with 0.1% glycerol, 0.4% malate, 0.25% casamino acids (CAA), and 25 μg of tryptophan/ml (Thomson et al., 1979). Yeast were grown on the following media: YPGE (Lam and Marmur, 1977I contained 1% yeast extract, 2% peptone, 3% glycerol, and 2% ethanol (±3% agar); glucose/CAA±tryptophan (50 μg/ml) contained per liter 6.7 g of yeast nitrogen base (without amino acids) (Difco), 20 g of glucose, ±30 g of Difco agar, 5 g of casamino acids (Difco), 60 mg of adenine, and 60 mg of uracil (Sherman et al., 1974); glycerol/ethanol/CAA±tryptophan contained the same but with 3% glycerol and 2% ethanol substituted for glucose.

Yeast Bank Construction

The yeast bank was made in E. coli strain JA221 by transformation with annealed recombinant plasmids consisting of ColE1 vector (EcoRI cut) with poly(dT) "Tails" and randomly sheared segments of yeast DNA with poly(dA) tails (Ratzkin and Carbon, 1977 PNAS USA 74: 487–491; Chinault and Carbon, 1979 Gene (Amst.) 5: 111–126). This library contains about 8000 individual colicin-E1-resistant colonies, of which 70 to 75% contain hybrid plasmids (15 kpb, average insert). These are stored in 96-well microtest II dishes (Falcon Plastics) at −80° C. in the presence of 8% dimethylsulfoxide in LB medium.

DNA Preparations and Transformation

Purification of covalently closed circular plasmid DNAs from E. coli (Clarke and Carbon, 1976) and transformation of E. coli (Clarke and Carbon, 1975 PNSA USA 71: 4361–4365) and yeast (Hsiao and Carbon, 1979 ibid 76: 3829–3833) with plasmid DNAs were performed as previously described. Yeast transformants were plated in 10 ml of regeneration agar containing 0.067 g of yeast nitrogen base, 1.64 g of Sorbitol, 0.2 g of glucose ($PgK^+$ selection), 0.3 g of agar, 0.05 g of casamino acids, 0.1 mg of adenine, and 0.2 mg of uracil (absence of tryptophan allowed $Trp^+$ selection).

Antibody Screening Procedures

Immunological screening was done as previously described (Method I. Clarke et al., 1979, Methods Enzymol. 68: 436–442; Hitzeman et al., 1979, in Eucaryotic Gene Regulation, Axel and Maniatas eds., Vol. 14, pp. 57–68 Academic Press, N.Y.). The screening procedure has been modified to help reduce the background of small specks and smears that are seen occasionally on the autoradiograms and to permit the screening of very small colonies (1000/plate) and phage plaques. Low backgrounds also give greater sensitivity since exposure times of 7 to 10 days instead of 2 days can be employed.

Background reduction is achieved by using a vacuum pump to deaerate the bovine serum albumin/glycine solution immediately before use. After 2 to 3 h at 37° C., the discs plus the bovine serum albumin/glycine are put in a cold room overnight and then heated at 37° C. for 3 to 4 h the next day before further use. Changes in gas solubility are believed to result in more even inactivation of unreacted CNBr-activated sites on the paper. After labeling with $^{125}$I-Ab and using the 5% calf serum/phosphate-buffered saline (0.14M NaCl solution) wash, the discs are suction washed with vacuum pump-deaerated (till no bubbles exit solution) phosphate-buffered saline. The final phosphate-buffered saline wash is also deaerated in this manner. It is also advantageous to filter the 5% calf serum solution containing $^{125}$I-Ab before addition of the discs. Millipore HA membrane filters, glass filters, and Nalgene sterilization filters (45 microns) have been used for this purpose.

Plasmid Reconstruction

Partial or complete restriction endonuclease digestions of plasmid DNAs were performed on 25 μg of plasmid in 200 μl of the appropriate buffer. Enzyme was inactivated at the proper time by adding 0.1 volume 200 mM EDTA, heating at 65° C. for 15 min, followed by one extraction with 50 μl of Tris-buffered phenol (pH 7) and two alcohol precipitations.

Six to ten micrograms of feragmented DNA from above were annealed in 10 mM Tris-HCl (pH 7.5) and 0.1M NaCl (90 μl total) for 20 h at 4° C. after first heating at 65° C. for 10 min. Five micrograms of partial Eco RI-cut pYe57E2 DNA plus 1 μg of the 1.4-kb Eco RI TRP1 fragment (Tschumper and Carbon, 1980 Gene (Amst.) 10: 157–166) were used for the experiment described below as 1, and 5 μg of HindIII-cut pBR322 DNA plus 5 μg of complete or partial HindIII-digested pYe57E2 DNA were used for the experiment described below as 2.

Experiment 1 is as follows. Plasmid DNAs were obtained using standard procedures from individual transformants obtained after partial EcoRI digestion of pYe57E2 DNA and ligation with the 1.4-kbp EcoRI TRP1 fragment (Stinchcomb, et al., 1979; Tschumper and Carbon, 1980) followed by transformation of strain JA300 (trp C117) and selection on Vogel's minimal citrate agar containing casamino acids plus thymine (tryptophan complementation). The transformant clones were screened using immunological screening method I, where high and low production of antigen was observed.

Experiment 2 is as follows. The transformants were obtained after partial or complete cutting of pYe57E2 DNA with HindIII and ligation with HindIII-cut pBR322 DNA. Transformants were selected by ampicillin resistance and screened by tetracycline sensitivity (either partial or complete) on S-agar plates. Antigen production was shown using immunological screening method I for the different transformant clones to be comparable to pYe57E2 or did not occur.

After annealing, 10 μg of bovine serum albumin (heat-treated at 65° C. for 20 min), 150 nmol of ATP, 0.5 μmol of dithiothreitol, and 0.5 unit of T4 ligase were added in 10 μl of solution followed by 10 μl of 600 mM Tris-HCl (pH 7.5), 10 mM EDTA, 100 mM MgCl$_2$. After 10 h at 10° C., the ligation mix was stored on ice until used for transformation.

3-Phosphoglycerate Kinase Assays on E. coli and Yeast Extracts

Five-hundred-milliliter cultures of yeast were grown at 30° C. (except SB-1225-1A, 23° C.) to an absorbance of 2 at 660 nm. After chilling on ice, each culture was centrifuged at 3,400×g for 20 min and the pellet was resuspended in ice-cold 0.15M KCl. After centrifuging again, each pellet was resuspended in 5 ml of extract buffer containing 2 mM 2-mercaptoethanol, 2 mM EDTA, 1 mM phenylmethylsulfonyl fluoride, and 50 mM potassium phosphate (pH 7.4). After freezing and thawing, extract was prepared in the French press using two passes at 16,000 p.s.i. Extracts were centrifuged at 16,000×g for 20 min and the supernatants were assayed for protein and 3-phosphoglycerate kinase activity.

E. coli strains were grown in 500 ml of VGM broth plus tryptophan (50 μg/ml) at 37° C. to an absorbance of 1 at 600 nm. After chilling on ice, cultures were centrifuged at 5,000×g for 20 min. The pellets were resuspended in 2 ml of 0.1M sodium phosphate (pH 7.5) containing 1 mM dithiothreitol, 0.1 mM EDTA, and 1 mM phenylmethylsulfonyl fluoride. After freezing and thawing at 37° C. (10 min), lysozyme was added at 100 μg/ml followed by a 20-min incubation at 37° C. Two freeze-thaws were used to aid in lysis. The extracts were sonicated gently to reduce viscosity and centrifuged at 10,000×g for 20 min. Supernatant were assayed for protein and 3-phosphoglycerate kinase activity.

Protein concentrations in the extracts were determined using the Bio-Rad reagent according to the method of Bradford (1976) Anal. Biochem. 72: 248–254). A standard solution from Bio-Rad containing bovine γ-globulin was used to obtain a standard curve.

3-Phosphoglycerate kinase assays were done spectrophotometrically at 30° C. measuring the change in absorbance at 340 nm as described by Scopes (1975 Methods Enzymol. 42: 134–138). A decrease in absorbance results from the oxidation of NADH in the presence of glyceraldehyde-3-phosphate dehydrogenae when coupled with the formation of 1,3-diphosphoglycerate by 3-phosphoglycerate kinase.

Containment Conditions

These experiments were carried out in conformance with the *National Institutes of Health Guidelines for Recombinant DNA Research.*

To obtain the PGK structural gene, a sample of purified yeast 3-phosphoglycerate kinase was used as an antigen to prepare antibody in rabbits for immunological screening of recombinant clone libraries. (Hitzeman et al., 1979, supra). When a collection of 4800 E. coli colonies from a hybrid plasmid yeast DNA clone library was screened by immunological method I using antibodies made to purified 3-phosphoglycerate kinase, one antigen-producing colony (57E2) was observed. The plasmid pYe57E2 was isolated from the clone and shown to contain a yeast DNA insert of about 15 kbp. This plasmid was used to transform E. coli strain JA221 (no ColE1 plasmid present) to colicin E1 resistance.

The 16-kbp yeast DNA segment inserted into the 6.3 kbp ColE1 vector was characterized by preparing a restriction map as indicated below.

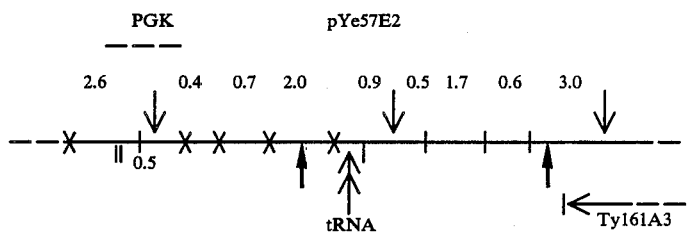

Detailed restriction map of the DNA insert in plasmid pYe57E2. Restriction sites are Eco RI (—|—); Bgl II (↓); HindIII (—X—); SalI (↑); XhoI (↔).

The conversion of plasmid pYe57E2 into a form capable of replicating autonomously in yeast, and thus giving a higher frequency of transformation, was accomplished by insertion into the plasmid of the 1,4-kbp EcoRI fragment from Yrp7, which contains the yeast TRP1 gene and a yeast chromosomal replicator (ars1) (Stinchcomb, et al., 1977). The insertion of the 1.4-kbp TRP1 fragment into pYe57E2 was previously described in the description referred to as Experiment 1. One plasmid, which was shown, as described previously, to produce antigens and designated pYe57E2(TRP1)-A4 was chosen to be the best candidate for obtaining a pgk trp1 yeast transformation since the TRP1 fragment is substituted for a small 0.6 kbp EcoRI fragment and this insertion is some distance (7 kbp) from the EcoRI site implicated in 3-phosphoglycerate kinase antigen production.

When plasmid pYe57E2(TRP1)-A4 DNA was used to transform a trp1-pgk yeast strain to Trp+ Pgk+, 20 TRP+ PGK+ transformants were obtained from 40 micrograms of DNA. When the same plasmid was used to transform yeast strain RH218 trp1 to TRP1+, 470 transformants were obtained/μg of DNA. Since a double selection for transformants were used, it is unlikely that the Pgk+ transformants were revertants. However, 8 of the transformants were further analyzed to determine whether the two phenotypes (TRP+ PGK+) were carried by a plasmid in the yeast transformants.

TABLE I

Two different transformants were examined in this manner as shown in Table II.

TABLE II

Specific Activities of 3-Phosphoglycerate Kinase in Yeast Transformant Extracts

| Yeast Strain | Relevant yeast genotype | Plasmid present | Relevant plasmid genotype |
|---|---|---|---|
| RH218 | trp1 | None | |
| SB5-6 | trp1 pgk | None | |
| SB5-8 | trp1 pgk | None | |
| SB5-6 | trp1 pgk | pYe57E2(TRP1)-A4 | TRP1+ PGK+ |
| SB5-8 | trp1 pgk | pYe57E2(TRP1)-A4 | TRP1+ PGK+ |
| RH218 | trp1 | pYe57E2(TRP1)-A4 | TRP1+ PGK+ |
| RH218 | trp1 | pLC544 | TRP1+ |
| SB-1225-1A | leu2 | None | |
| SB-1225-1A | leu2 | pM3 | LEU2+ PGK+ |
| SB-1225-1A | leu2 | pM3 | LEU2+ PGK+ |

| Yeast Strain | Extract specific activities[a] | | | Percentage of cells retaining plasmid Preparation 3[b] | Normalized specific activity[c] |
|---|---|---|---|---|---|
| | Preparation 1 | Preparation 2 | Preparation 3 | | |
| RH218 | 14 | 13 | 9.4 | | |
| SB5-6 | | | 0.02 | | |
| SB5-8 | | | 0.01 | | |
| SB5-6 | 8.1 | 5.8 | 3.3 | 20 | 16 |
| SB5-8 | 8.3 | 6.6 | 4.8 | 40 | 12 |
| RH218 | | 20 | 16 | 50 | 22 |
| RH218 | | 11 | 9.0 | 14 | |
| SB-1225-1A | | | 9.5 | | |
| SB-1225-1A | | | 19 | 48 | 29 |
| SB-1225-1A | | | 16 | 29 | 32 |

[a]3-Phosphoglycerate kinase assays and protein assays are described under "Experimental Procedures." Specific activities are in micromoles of 3-phosphoglycerate phosphorylated/min at 30° C./mg of extract protein. Each value represents the averages of at least three 3-phosphoglycerate kinase assays and three protein assays. All values show a standard deviation of about ±10%, except for the values of 0.01 and 0.02. Three sets of extracts were prepared in the same manner on different dates as described under "Experimental Procedures."
[b]The fraction of cells retaining plasmid was determined by plating the cells used for extract preparation on selective and nonselective media for the genetic marker on the plasmid and scoring the relative numbers of colonies. For strains SB5-6 and SB5-8, selective plates were glycerol/ethanol/CAA. For strain RH218, selective plates were glucose/CAA and nonselective plates were glucose/CAA plus tryptophan. For strain SB-1225-1A, growth was at 23° C., selective plates contained glucose plus tryptophan and adenine, while nonselective plates also contained leucine.
[c]Normalized to 0% segregation.

Segregation of TRP1+ and PGK+ from yeast clones transformed with pYe57E2(TRP1)-A4 DNA

| Transformant clone No.[a] | trp1− pgk− | TRP1+ PGK+ | Segregation frequency % |
|---|---|---|---|
| 1 | 106/106 | 0/106 | >99 |
| 2 | 60/63 | 3/63 | 95 |
| 3 | 100/100 | 0/100 | >99 |
| 4 | 87/88 | 1/88 | 99 |
| 5 | 300/300 | 0/300 | >99 |
| 6 | 118/216 | 98/216 | 55 |
| 7 | 196/206 | 10/206 | 95 |
| 8 | 210/222 | 12/222 | 95 |

[a]The eight TRP1+ PGK+ transformants were first streaked out on nonselective media (YPGE plus tryptophan), then replicaplated to selective media (glycerol/ethanol/CAA for tryptophan selection, glucose/CAA plus tryptophan for Pgk+ selection, and glucose/CAA for double selection) to score for segregation. No trp1− PGK+ or TRP1+ pgk− segregants were detected.

Autonomously replicating plasmids containing the ars1 replicator are mitotically unstable and are readily lost by segregation in the absence of selective pressure. In the yeast genome, these two markers are normally present on different chromosomes (trp1 on IV and pgk on III) and are thus unlinked. However, when the transformants were streaked out on non-selective media followed by replica plating onto selective media to score for segregants, both Trp+ and Pgk+ phenotypes were lost together (see Table I). Thus the two genes were shown to behave as if they were linked on a plasmid. The data support that the plasmid contains the yeast PGK locus and that this gene is a structural gene for yeast 3-phosphoglycerate kinase.

The expression of the PGK gene was shown by assaying 3-phosphoglycerate kinase enzyme activity in trp1 pgk yeast as well as in Trp1+ Pgk+ transformants. If the enzyme levels are normalized to 0 segregation, the specific activities will be 1.3 to 1.7 times the normal wild-type level. Thus it appears that the PGK gene carried by the plasmid is being expressed at a slightly higher level than when present in the genome; however, the copy number of plasmids of this type could be somewhat greater than 1 on the average. The pYe5-7E2(TRP1)-A4 plasmid in normal Pgk+ hyeast (RH218) expresses enzyme at the level expected by the summation of that produced from the chromosomal gene and the plasmid-carried gene, indicating the absence of any controls regulating the absolute level of 3-phosphoglycerate kinase in the cell.

A plasmid (pM3) containing the 3.1-kbp HindIII fragment from pYe57E2 carries the information necessary for expression of 3-phosphoglycerate kinase from the cloned DNA segment in yeast (see Table II). This plasmid contains the vector pBR322 with a 2.4-kbp pstI fragment including the yeast LEU2 gene (Strathern et al. (1980) Cell 18: 309-319). As shown in Table II, PGK+ yeast transformants containing this plasmid possess nearly two-fold elevated levels of 3-phosphoglycerate kinase activity, indicating that the enzyme can be synthesized to reasonable high levels from the aforementioned fragment. Since the coy number of pM3 is unknown, the exact level of enzyme expression from the clone PGK gene is uncertain.

A further plasmid was prepared by introducing the 3.1 kbp HindIII fragment containing the PGK locus into the HindIII site of plasmid YEp13 (Broach et al. (1979) Gene 8: 121-133). The new plasmid pY9, depicted in FIG. 1, possesses a number of advantages.

First, this plasmid contains yeast replicator sequences from the natural 2μ-plasmid and therefore exists in th yeast cell in multiple copies, boosting the production of PGK controlled gene products 7 to 10 times over what would be found in normal yeast (single copy). Secondly, selected conditions can identify pY9 in yeast by complementing Leu2 mutations (Hinnen et al. (1978) PNAS USA 75: 1929-1933). In addition, selected conditions can also be used for manipulation of pY9 in bacteria with both the ampicillin resistance gene from pBR322 and the LeuB mutation complementation (Ratzkin and Carbon (1977) ibid. 74: 487-491). The plasmid may be used in the same manner described previously for providing a restriction site for introduction of structural genes to be under the regulatory control of the PGK regulatory genes. A foreign DNA fragment containing the gene to be expressed and its translational start signal (like a cDNA copy of a gene) is ligated into the synthetic site. Plasmids that contain intact PGK transcription signals and the inserted gene in the correct orientation will synthesize a foreign gene product in yeast.

A foreign gene may be introduced into a vector such as pY9 as follows. The vector is cleaved by partial or complete digestion, depending on the endonuclease, with a restriction endonuclease, such as KpnI, XbaI or other endonuclease indicated previously employing the conditions of the supplier. Restriction occurs within the PGK structural gene and also at some point upstream from the promoter distal to the HindIII site to provide DNA segments cleaved about 600 bp-1000 bp from the HindIII cleavage site of the 3.1 kbp fragment at the 3'-terminus of the coding strand. The enzyme is then inactivated and the desired DNA is isolated as described. The DNA segments (20 μg/ml) are incubated with Ps. nuclease BAL 31 (130 unites/ml) at 30° C. in buffer (12.5 mM MgSO$_4$, 12.5 mM CaCl$_2$, 0.2M NaCl, 1 mM EDTA, and 20 mM Tris-HCl (pH8.1)) and aliquots removed at varying times. The reaction is stopped by the addition of 3.5 μl 0.1M EDTA (pH8.1).

Linkers are ligated to the digested DNA segments by combining DNA fragments of 12 bp having, for example, a sequence cleaved by EcoRI or BamHI. The linkers are ligated to the DNA segments by combining about 5 μg of the DNA segments to about a five mole excess of the linkers in a solution of 10 μg of bovine serum albumin (heat-treated at 65° C. for 20 min), 150 nmol of ATP, 0.5 μmol of dithiothreitol and 0.5 unit of T4 ligase in 10 μl of solution (10 mM Tris-HCl (pH7.5), 0.1M NaCl). Ten μl of 0.6M Tris-HCl (pH7.5), 10 mM EDTA and 100 mM MgCl$_2$ were added and after 10 h at 10° C. the mixture is stored at 0° C. The resulting DNA is then cleaved with EcoRI and HindIII or BamHI and HindIII under conditions indicated by the supplier and the DNA segments isolated as described. Each of the resulting DNA segments contains a HindIII terminus and a BamHI or EcoRI terminus. The former segments (HindIII/BamHI termini) are then ligated into the HindIII and BamHI site of plasmid YEp13, while the latter (HindIII/EcoRI termini) may be ligated into a different yeast plasmid having the appropriate restruction sites.

A structural gene is inserted into the EcoRI or BamHI site, having complementary cohesive ends with the cohesive end at the 3'-terminus of the coding strand adjacent the f-met codon and with the 5'-terminus downstream from the ribosomal stop site. In other words, the gene which is selected is inserted in the correct orientation for regulation by the PGK regulatory signals. Also, a transcription terminator can be provided by adding a BglII-BamHI DNA fragment containing the PGK terminator signals by partial digestion of the plasmid with BamHI and insertion of the terminator containing fragment into the BamHI site. One then selects for the plasmid having the terminator at the correct BamHI site and in the correct orientation by hybridization, e.g., Southern blotting or by employing antibodies to the protein expressed by the foreign gene. After ligation as described previously, the circularized DNA is used for transformation of a yeast host and isolation of transformants expressing the structural gene is achieved by detection in conventional ways, depending upon the expression product. Where an enzyme is expressed, the enzymatic activity can be determined. Peptides can be determined immunologically and, as apporopriate, assayed for physiological activity.

It is evident from the above results that plasmids are provided which yield high levels of expression of a structural gene, particularly the PGK gene. Furthermore, by simpl genetic manipulation, various structural genes can be inserted to replace the PGK gene and be expressed under the regulatory control of the PGK promoter and other regulatory genes. Thus, an efficient vector is provided which provides for a convenient restriction site for insertion of structural genes whose transcription and expression is under the regulatory control of the regulatory genes of the yeast PGK gene.

Although the foregoing invention has been described in some detail by way of illustration and example for purposes of clarity of understanding, it will be obvious that certain changes and modifications may be practiced within the scope of the appended claims.

What is claimed is:

1. A vector useful for expression of a structural gene in *Saccharomyces cerevisiae* comprising the *Saccharomyces cerevisiae* 2μ-replication system, a yeast chromosomal replicator, the structural gene including its leader region and the regulatory genes of the *Saccharomyces cerevisiae* PGK gene and having a restriction site intermediate the promoter and terminator of said PGK gene.

2. A vector according to claim 1, wherein said restriction site is in the leader region of said PGK gene.

3. A novel *Saccharomyces cerevisiae* yeast vector comprising:
   a *Saccharomyces cerevisiae* 2 micron extrachromosomal replication system; and
   a DNA fragment of *Saccharomyces cerevisiae* comprising the structural gene for PGK and the regulatory signals for the PGK structural gene including its promoter and terminator.

4. A novel *Saccharomyces cerevisiae* yeast vector comprising:
   a *Saccharomyces cerevisiae* 2 micron extrachromosomal replication system; and
   a DNA fragment comprising the structural gene for a *Saccharomyces cerevisiae* PGK and the regulatory signals including its promoter and terminator of said PGK structural gene.

5. The novel vector according to claim 4, further comprising:
   a restriction site located intermediate the promoter and terminator of said PGK structural gene.

6. The novel vector according to claim 3, further comprising:
   a restriction site located intermediate the promoter and terminator of said PGK structural gene.

7. A novel *Saccharomyces cerevisiae* yeast vector comprising:
   a *Saccharomyces cerevisiae* extrachromosomal replication system; and a 3.1 kbp HindIII fragment of *Saccharomyces cerevisiae* containing the PGK structural gene and its regulatory signals including the promoter and terminator.

8. The yeast vector according to claim 7, wherein a restriction site is located intermediate the promoter and terminator of said PGK structural gene.

9. The yeast vector according to claim 7, further comprising at least one selectable yeast marker gene.

10. The yeast vector according to claim 9, wherein said selectable yeast marker gene is LEU2 or TRP1.

11. Plasmid pY9.

12. The novel yeast vector according to claim 5, further cpomprising a yeast chromsomal replicator.

13. The novel yeast vector according to claim 12, wherein said chromsomal replicator is arsl.

14. The novel yeast vector according to claim 12, wherein said chromsomal replicator is joined to a second structural gene.

15. The novel yeast vector according to claim 4, further comprising at least one selectable yeast marker gene.

16. The novel yeast vector according to claim 14, wherein said selectable yeast marker gene is LEU2 or TRP1.

17. Plasmid pM3.

18. A vector according to claim 6, wherein said restriction site is in the leader region of said PGK gene.

19. A vector according to any one of claims 6, 8 or 18, wherein said restriction site is a unique restriction site.

* * * * *